US011607133B2

(12) United States Patent
Eom et al.

(10) Patent No.: US 11,607,133 B2
(45) Date of Patent: Mar. 21, 2023

(54) BIOLOGICAL COMPONENT MEASURING APPARATUS AND BIOLOGICAL COMPONENT MEASURING METHOD

(71) Applicant: SAMSUNG ELECTRONICS CO., LTD., Suwon-si (KR)

(72) Inventors: Kun Sun Eom, Yongin-si (KR); Joon Hyung Lee, Seongnam-si (KR); Jeong Eun Hwang, Suwon-si (KR); Jung Yong Nam, Hwaseong-si (KR); Ki Young Chang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 167 days.

(21) Appl. No.: 17/239,047

(22) Filed: Apr. 23, 2021

(65) Prior Publication Data

US 2021/0235990 A1 Aug. 5, 2021

Related U.S. Application Data

(63) Continuation of application No. 16/173,695, filed on Oct. 29, 2018, now Pat. No. 11,013,412.

(30) Foreign Application Priority Data

Dec. 29, 2017 (KR) .................. 10-2017-0184312

(51) Int. Cl.
*A61B 5/1455* (2006.01)
*A61B 5/00* (2006.01)
(Continued)

(52) U.S. Cl.
CPC .......... *A61B 5/0059* (2013.01); *A61B 1/0638* (2013.01); *A61B 5/02007* (2013.01);
(Continued)

(58) Field of Classification Search
CPC .............. A61B 5/0059; A61B 5/14546; A61B 5/14532; A61B 5/1455; A61B 5/7225
See application file for complete search history.

(56) References Cited

U.S. PATENT DOCUMENTS 6,026,314 A 2/2000 Amerov et al.
6,061,583 A 5/2000 Ishihara et al.
(Continued)

FOREIGN PATENT DOCUMENTS

CA 2 610 249 A1 12/2006
CN 1206339 A 1/1999
(Continued)

OTHER PUBLICATIONS

Communication dated Oct. 26, 2022, issued by the China National Intellectual Property Administration in Chinese Application No. 201811322243.1.
(Continued)

*Primary Examiner* — Eric F Winakur
(74) *Attorney, Agent, or Firm* — Sughrue Mion, PLLC

(57) ABSTRACT

A biological component measuring apparatus may include: a first light source configured to emit a first light of a first wavelength range onto an object; a second light source configured to emit a second light of a second wavelength range onto the object, the second wavelength range being different from the first wavelength range; a detector configured to detect the first light and the second light which are scattered from the object; and a processor configured to determine a scattering coefficient based on the detected first light, obtain blood vessel depth information based on the detected second light, and measure a biological component by correcting the scattering coefficient based on the blood vessel depth information.

20 Claims, 11 Drawing Sheets

(51) Int. Cl.
  *G01N 21/17* (2006.01)
  *A61B 1/06* (2006.01)
  *A61B 5/02* (2006.01)
  *A61B 5/145* (2006.01)

(52) U.S. Cl.
  CPC ........ *A61B 5/1455* (2013.01); *A61B 5/14532* (2013.01); *A61B 5/14546* (2013.01); *A61B 5/7225* (2013.01); *G01N 21/17* (2013.01); *A61B 2562/046* (2013.01)

(56) References Cited

U.S. PATENT DOCUMENTS

| | | | |
|---|---|---|---|
| 7,415,139 | B2 | 8/2008 | Takiguchi |
| 7,869,624 | B2 | 1/2011 | Takiguchi |
| 8,144,942 | B2 | 3/2012 | Takiguchi |
| 8,260,016 | B2 | 9/2012 | Maeda et al. |
| 8,811,680 | B2 | 8/2014 | Takiguchi |
| 9,234,842 | B2 | 1/2016 | Takiguchi |
| 10,045,722 | B2 | 8/2018 | Kintz et al. |
| 10,371,629 | B2 | 8/2019 | Takiguchi |
| 10,542,920 | B2 | 1/2020 | Sato |
| 11,134,871 | B2 | 10/2021 | Kintz et al. |
| 2005/0180620 | A1 | 8/2005 | Takiguchi |
| 2006/0058595 | A1 | 3/2006 | Herrmann |
| 2007/0252984 | A1 | 11/2007 | Van Beek et al. |
| 2010/0042005 | A1 | 2/2010 | Bigio et al. |
| 2010/0054576 | A1 | 3/2010 | Tsujita |
| 2011/0276276 | A1 | 11/2011 | Kashyap et al. |
| 2012/0209094 | A1 | 8/2012 | Schurman et al. |
| 2012/0253122 | A1 | 10/2012 | Minetoma et al. |
| 2014/0323831 | A1 | 10/2014 | Sato |
| 2015/0313516 | A1 | 11/2015 | Shimizu et al. |
| 2017/0135616 | A1 | 5/2017 | Sato |
| 2017/0150931 | A1 | 6/2017 | Lee et al. |
| 2019/0208986 | A1 | 7/2019 | Saito |
| 2022/0095960 | A1 | 3/2022 | Kintz et al. |

FOREIGN PATENT DOCUMENTS

| | | |
|---|---|---|
| CN | 105120750 A | 12/2015 |
| CN | 106163399 A | 11/2016 |
| EP | 2 930 495 A1 | 10/2015 |
| JP | 2007-117221 A | 5/2007 |
| JP | 2013-126510 A | 6/2013 |
| JP | 2014-124454 A | 7/2014 |
| JP | 2014-124455 A | 7/2014 |
| JP | 2016-106870 A | 6/2016 |
| JP | 6029128 B1 | 11/2016 |
| KR | 10-1491853 B1 | 2/2015 |
| WO | 03/096272 A1 | 11/2003 |
| WO | 2014/087825 A1 | 6/2014 |
| WO | 2015/151587 A1 | 10/2015 |
| WO | 2017/119130 A1 | 7/2017 |

OTHER PUBLICATIONS

Communication dated Apr. 11, 2019, issued by the European Patent Office in counterpart European Application No. 18248009.5.
Tianchen Shi et al., "Multispectral method for skin imaging: development and validation", Applied Optics, vol. 46, No. 36, Optical Society of America, XP001510547, Dec. 20, 2007, pp. 8619-8626.
Communication dated Jun. 7, 2022, issued by the Japanese Patent Office in Japanese Patent Application No. 2018-231769.

BIOLOGICAL COMPONENT MEASURING APPARATUS AND BIOLOGICAL COMPONENT MEASURING METHOD

CROSS-REFERENCE TO RELATED APPLICATION(S)

This is a continuation application of U.S. application Ser. No. 16/173,695, filed Oct. 29, 2018, which claims priority from Korean Patent Application No. 10-2017-0184312, filed on Dec. 29, 2017 in the Korean Intellectual Property Office, the disclosures of which are incorporated herein by reference in their entireties.

BACKGROUND

Field

Apparatuses and methods consistent with exemplary embodiments relate to measuring biological components in a non-invasive manner, and more particularly to measuring biological components by emitting light and detecting light signals.

Description of the Related Art

Triglyceride levels are increased by obesity, lack of exercise, smoking, and the like. The triglyceride concentration in the blood should be managed, as high triglyceride levels are generally associated with metabolic syndrome and may be a risk factor for atherosclerosis. By using an invasive method to measure triglyceride levels in the body, the triglyceride concentration can be measured accurately, but the method may cause psychological and physical pain, making it difficult to regularly monitor triglyceride levels for health management.

Thus, research has been conducted on techniques for using scattered light in a non-invasive biological component measuring apparatus. For example, biological components may be estimated by emitting light from a light source to skin and measuring, by a detector, an intensity of scattered light, which is scattered from the skin after being emitted thereto, based on a distance between the light source and the detector.

SUMMARY

According to an aspect of an exemplary embodiment, there is provided a biological component measuring apparatus including: a first light source configured to emit a first light of a first wavelength range onto an object; a second light source configured to emit a second light of a second wavelength range onto the object, the second wavelength range being different from the first wavelength range; a detector configured to detect the first light and the second light which are scattered or reflected from the object; and a processor configured to determine a scattering coefficient based on the detected first light, obtain blood vessel depth information based on the detected second light, and measure a biological component by correcting the scattering coefficient based on the blood vessel depth information.

The first light source and the detector may be disposed on a surface of the object to be aligned with a position of at least one blood vessel of the object.

The biological component measuring apparatus may further include a plurality of detectors comprising the detector, wherein the plurality of detectors may be disposed at different distances from the first light source.

The second light source may be spaced apart from the detector by a predetermined distance.

The second wavelength range may be from 500 nm to 855 nm.

The first light source and the second light source may include at least one of a light emitting diode (LED), a laser diode, and a fluorescent body.

The first light source may be further configured to emit a plurality of first lights including the first light, wherein the plurality of detectors may be configured to detect the plurality of first lights which are scattered from the object, and wherein the processor may be further configured to select one or more detectors of the plurality of detectors based on at least one of a light intensity of the detected plurality of first lights, a signal to noise ratio (SNR) of the detected plurality of first lights, a distance between the first light source and each of the plurality of detectors, and blood vessel depth information for each of the plurality of detectors.

The processor may be further configured to select the one or more detectors in response to determining that the one or more detectors are aligned with blood vessels having a same depth from a skin surface of the object, and determine the scattering coefficient based on one or more first lights of the plurality of first lights which are detected by the selected one or more detectors.

The biological component measuring apparatus may further include a plurality of first light sources configured to emit a plurality of first lights including the first light, wherein the plurality of detectors may be configured to detect the plurality of first lights which are scattered from the object, and wherein the processor may be further configured to calculate a signal to noise (SNR) ratio of the detected plurality of first lights, select one or more first light sources of the plurality of first light sources in order of magnitudes of the SNR, and select one or more detectors of the plurality of detectors in the order of magnitudes of the SNR.

The process may be further configured to determine a detection depth of the detected first light based on the blood vessel depth information, and correct the scattering coefficient based on a result of comparison of the detection depth with a reference depth The processor may be further configured to determine a scattered light intensity based on the detected first light, and determine the scattering coefficient based on the scattered light intensity and a distance between the detector and the first light source.

The processor may be further configured to calculate a reflected light intensity based on the detected second light, and generate the blood vessel depth information by estimating a change in blood vessel depth according to a change in the reflected light intensity.

The first light source, the second light source, and the detector may be arranged in a predetermined array structure having a square shape, a circular shape, a concentric circular shape, or a band shape.

The biological component measuring apparatus may further include an output interface configured to output at least one of an operation state of the first light source, the second light source, and the detector, a position and a depth of blood vessels, a scattered light intensity, a reflected light intensity, a type and a concentration of a biological component, guide information, and warning information.

The biological component may include triglyceride, cholesterol, proteins, blood glucose, and uric acid.

According to an aspect of another exemplary embodiment, there is provided a biological component measuring apparatus including: a light source array configured to emit a light onto an object; a detector array configured to detect the light emitted by each light source of the light source array; and a processor configured to individually drive each light source included in the light source array, generate information of a light path length between the driven light source and each detector of the detector array based on the light detected by each detector of the detector array, and measure a biological component by correcting a scattering coefficient based on the information of the light path length.

The processor may be further configured to individually control each detector of the detector array to drive one or more detectors of the detector array.

The processor may be further configured to perform comparison between the information of the light path length and reference light path length information, and correct the scattering coefficient based on the comparison.

The processor may be further configured to select two or more detectors of the detector array based on the information of the light path length, and determine the scattering coefficient based on the light detected by the selected two or more detectors.

Each light source of the light source array and each detector of the detector array may be arranged in a predetermined array structure having a shape among a square shape, a circular shape, a concentric circular shape, or a band shape.

According to an aspect of another exemplary embodiment, there is provided a biological component measuring method including: detecting, by a detector, a first light signal emitted by a first light source; detecting, by the detector, a second light signal emitted by a second light source; calculating a scattering coefficient based on the detected first light signal; obtaining blood vessel depth information based on the detected second light signal; correcting the scattering coefficient based on the blood vessel depth information; and measuring a biological component based on the corrected scattering coefficient.

The first light source and the detector may be disposed to be aligned with a position of at least one blood vessel.

The second light source may emit light in a wavelength range of 500 nm to 855 nm.

The detector may be of a plurality of detectors, and the biological component measuring method may further include selecting one or more detectors of the plurality of detectors based on at least one of a light intensity of the first light signal and the second light signal which are detected by each detector of the plurality of detectors, a signal to noise ratio (SNR) of the first light signal and the second light signal which are detected by each detector of the plurality of detectors, a distance between the first light source and each detector of the plurality of detectors, and blood vessel depth information for each detector of the plurality of detectors.

The selecting the one or more detectors may include selecting the one or more detectors in response to determining that the one or more detectors are disposed aligned with blood vessels having a same depth from a skin surface.

The first light source may be of a plurality of first light sources, and the biological component measuring method may further include: calculating a signal to noise (SNR) ratio of the first light signal detected by each detector of the plurality of detectors; and selecting one or more first light sources of the plurality of first light sources in order of magnitudes of the SNR of the first light signal, wherein the selecting the one or more detectors may include selecting the one or more detectors in the order of magnitudes of the SNR.

The correcting the scattering coefficient may include: determining a detection depth of the first light signal based on the blood vessel depth information; and correcting the scattering coefficient based on a result of comparison of the detection depth with a reference depth.

The determining the scattering coefficient may include: calculating a scattered light intensity based on the first light signal; and calculating the scattering coefficient based on the scattered light intensity and a distance between the detector and the first light source.

The obtaining the blood vessel depth information may include: calculating a reflected light intensity based on the second light source; and generating the blood vessel depth information by estimating a change in blood vessel depth according to a change in the light intensity.

According to an aspect of another exemplary embodiment, there is provided a biological component measuring apparatus including: a light source configured to emit a first light of a first wavelength range and a second light of a second wavelength range to an object; a detector configured to detect the first light and the second light which are scattered or reflected from the object; and a processor configured to measure a scattering coefficient of the detected first light, obtain depth information of a blood vessel of the object based on a reflected light intensity of the detected second light, and determine a triglyceride level of the object based on the scattering coefficient and the depth information of the blood vessel.

The second wavelength range may be greater than the first wavelength range.

The processor may be further configured to obtain the depth information of the blood vessel based on a relationship between a change in blood vessel depth and a change in the reflected light intensity

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
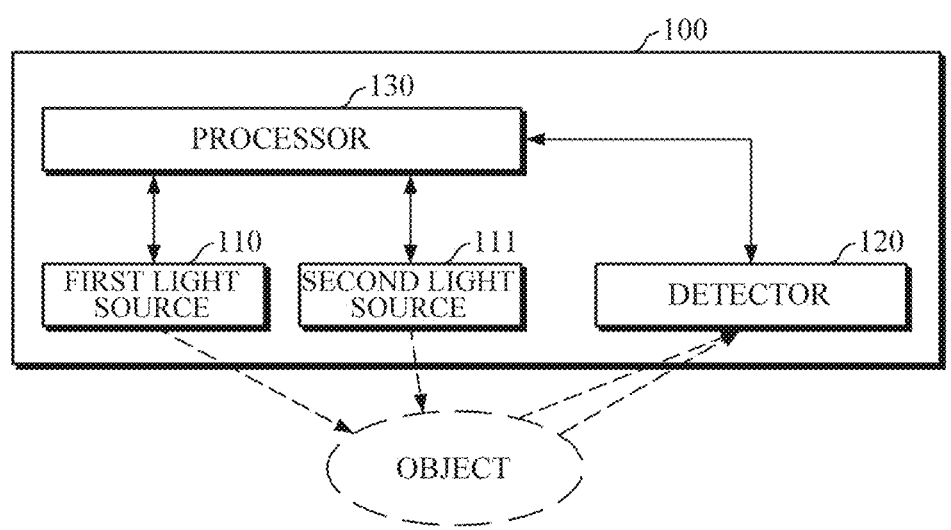
FIG. 1 is a block diagram illustrating a biological component measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating a biological component measuring apparatus according to an exemplary embodiment.

The biological component measuring apparatus 100 may include a first light source 110, a second light source 111, a detector 120, and a processor 120. The processor 130 may include one or more processors, memories, and a combination thereof. The first light source 110 and the second light source 111 may emit light onto an object, and the detector 120 may receive the light when the emitted light is reflected, deflected, or scattered from a biological component contained in the blood of blood vessels of the object. The processor 120 may control to measure a scattered light intensity of the light received by the detector 120, and may determine a concentration of the biological component based on the scattered light intensity and a distance between the first and the second light sources 110 and 111 and the detector 120. Here, the biological component may include at least one of triglyceride, cholesterol, proteins, blood glucose, and uric acid, and may include various biological components which are present only inside or outside the blood vessels according to sizes and types of particles.

The biological component measuring apparatus 100 may correct the measured concentration of a biological component based on blood vessel depth information.

For example, the biological component measuring apparatus 100 may emit light onto an object, and may estimate a blood vessel depth based on a change in a signal intensity of reflected light according to a change in blood vessel depth. The biological component measuring apparatus 100 may measure the concentration of a biological component based on a detected scattered light signal; and if there is a change in the measured concentration of the biological component, biological component measuring apparatus 100 may determine, based on blood vessel depth information, whether the concentration of the biological component is actually changed or the concentration of the biological component is measured differently due to the change in blood vessel depth.

In this case, upon determining that the change in the measured concentration of the biological component is caused by the change in blood vessel depth, the biological component measuring apparatus 100 may correct the concentration of the biological component based on the generated blood vessel depth information.

As described above, by correcting the measured concentration of the biological component based on the blood vessel depth information of the object, the biological component measuring apparatus 100 may correct a measurement error caused by an external factor, and thus may measure biological components accurately.

According to another exemplary embodiment, the first light source 110 and the second light source 120 may be implemented as a single light source configured to emit light of different wavelengths. For example, the single light source may emit a light having a relatively long wavelength (e.g., a red light) to measure the blood vessel depth because a long wavelength light tends to be sensitive to the change of the blood vessel depth but rarely affected by the change of triglyceride concentration. In another example, the single light source may use the same wavelength to measure the blood vessel depth and the light scattering coefficient.

Hereinafter, measurement of a biological component by the biological component measuring apparatus 100 will be described in detail with reference to FIGS. 1, 2, 3A, and 3B.

Figure 2:
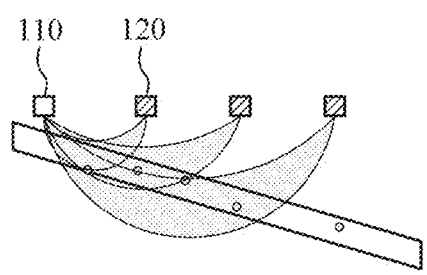
FIG. 2 is a diagram explaining an operation of calculating a scattering coefficient by a biological component measuring apparatus according to an exemplary embodiment.
Figure 3A:
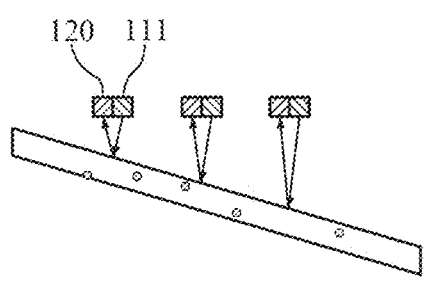
FIG. 3A is a diagram explaining an operation of calculating blood vessel depth information by a biological component measuring apparatus according to an exemplary embodiment.
Figure 3B:
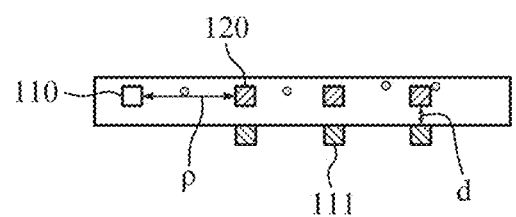
FIG. 3B is a diagram explaining an operation of calculating blood vessel depth information by a biological component measuring apparatus according to another exemplary embodiment.

FIG. 2 is a diagram explaining an operation of calculating a scattering coefficient by a biological component measuring apparatus according to an exemplary embodiment. FIGS. 3A and 3B are diagrams explaining an operation of calculating a blood vessel depth by a biological component measuring apparatus according to various exemplary embodiments.

The first light source 110 and the second light source 111 may emit light onto an object. In this case, the first light source 110 and the second light source 111 may emit light in a specific wavelength band of visible light, or may emit light in a near infrared range (e.g., 0.75-1.4 µm) or a mid infrared range (e.g., 3-8 µm).

Hereinafter, for convenience of explanation, description will be made based on an example where the first light source 110 emits light in a near infrared wavelength region, and the second light source 111 emits light in a predetermined wavelength region (e.g., light in a Green to Infrared region in a wavelength range of 500 nm to 855 nm). However, a light wavelength region of the first light source 110 may be the same as or different from that of the second light source 111, and the light wavelength region is not limited to a specific wavelength region. Further, a light wavelength region for measuring a scattering coefficient may be separated from a light wavelength region for estimating a blood vessel depth.

In an exemplary embodiment, the second light source 111 according to an exemplary embodiment may be configured to emit red light (e.g., light in a wavelength range of 630 nm to 780 nm, etc.) to provide information about a blood vessel depth. For example, the second light source 111 may be implemented as a red light-emitting diode which emits a red light toward a skin surface so that the red light propagates to a blood vessel underneath the skin surface and then is reflected or scattered from components of the blood vessel (e.g., intralipid, triglyceride, etc.). The detector 120 may detect a light signal which carries the red light reflected or scattered from the blood vessel components, and the processor 130 may determine a depth of the blood vessel from the skin surface based on an intensity (e.g., a voltage level) of the detected light signal. In particular, the biological component measuring apparatus 100 may store information about a relationship between a blood vessel depth and a voltage level of a detected light signal. For example, the biological component measuring apparatus 100 may store a graph or an equation indicating that the blood vessel depth is in inverse proportion to the voltage level of the detected light signal. With reference to the graph, the processor 130 may determine the depth of the blood vessel by applying the voltage level of the light signal detected by the detector 120 to the graph or equation.

In addition, the first light source 110 and the second light source 111, which are light sources physically independent of each other, may emit light in a specific wavelength band, but may also be light sources emitting light in multiple wavelength bands.

The detector 120 may receive light emitted by the multiple light sources 110 and 111.

Here, the detector 120 may include a photo diode, a photo transistor (PTr), or a charge-coupled device (CCD), but is not limited thereto. For example, the detector 120 may detect, as a light signal, at least one of reflected light which is reflected from skin of an object, absorbed light which is absorbed into the skin, and scattered light which is scattered from a biological component, after light is emitted from the multiple light sources.

Further, the detector 120 may be one or more in number, which may be arranged in a predetermined array structure, and may be spaced apart by a predetermined distance from the multiple light sources 110 and 111. Hereinafter, for convenience of explanation, a light signal may refer to a signal of light which is detected by the one or more detectors 120 after being emitted by the multiple light sources 110 and 111 and is scattered and/or reflected from a biological component.

Moreover, for convenience of explanation, a first light signal may refer to a scattered light signal which is scattered from a biological component in the blood of blood vessels of an object after light is emitted by the first light source, and a second light signal may refer to a reflected light signal which is reflected from the blood vessels of the object. However, the first light signal and the second light signal are not limited thereto, and the first light signal may be a light signal for measuring a biological component of an object, and the second light signal may be a light signal for generating blood vessel depth information.

In addition, the detector 120 may be one or more in number, which may be arranged in a predetermined array structure, and may be spaced apart by a predetermined distance from the first light source 110 and the second light source 111.

For example, referring to FIGS. 1, 3A, and 3B, the second light source 111 may be spaced apart from the detector 120 by a predetermined distance d; and in the case where there are a plurality of detectors 120 and a plurality of second light sources 111, the second light sources 111 may be disposed on the side of each of the plurality of detectors.

That is, in order to determine the depth from the skin surface of the object to blood vessels, the second light sources 111 are disposed to have a predetermined distance d from the corresponding detectors 120, respectively.

A plurality of detectors 120 may be disposed at different distances from the first light source. In the case where the biological component measuring apparatus 100 measures a biological component based on a scattering coefficient, the biological component measuring apparatus 100 may calculate a scattering coefficient based on the first light signal and a distance between the first light source 110 and the detector 120, and may estimate the concentration of a biological component based on the calculated scattering coefficient.

For example, the detector 120 may include a first detector and a second detector which are disposed at different distances from the first light source, and the biological component measuring apparatus 100 may calculate the scattering coefficient based on a light intensity of the first light signal; and a distance $\rho_1$ between the first light source and the first detector and a distance $\rho_2$ between the first light source and the second detector.

In this case, the number of detectors 120 may vary according to a computation capability of the processor 130, and power consumption and types of a device in which the biological component measuring apparatus 100 is mounted, but the number thereof is not limited thereto.

The first light source 110 and the detector 120 may be disposed on the surface of an object to be aligned with a position of the blood vessels. For example, the first light source 110 may be arranged side by side along the blood vessels on the surface of the object, and the detector 120 may be arranged side by side along the blood vessels at a position spaced apart by a predetermined distance from the first light source 110.

Further, the first light source 110, the second light source 111, and the detector 120 may be one or more in number. In the case where there are a plurality of first light sources 110, second light sources 111, and detectors 120, the first light sources 110, the second light sources 111, and the detectors 120 may be arranged in a predetermined array structure. For example, the first light source 110, the second light source 111, and the detector 120 may be arranged in a predetermined array structure having one or more of a square shape, a circular shape, a concentric circular shape, and a band shape.

The processor 130 may calculate a scattering coefficient based on the detected first light signal, may calculate blood vessel depth information based on the detected second light signal, and may correct the scattering coefficient based on the calculated blood vessel depth information.

Referring to FIGS. 1, 2 and 3A, the processor 130 may calculate a light intensity of the first light signal based on the first light signal detected by the detector 120. Upon calculating the light intensity, the processor 130 may calculate the scattering coefficient based on the light intensity of the first light signal, and a distance P between the first light source 110 and the detector 120. In the case where there are two or more detectors 120, the processor 130 may calculate the scattering coefficient based on a distance between the first light source 110 and each of the detectors 120, and the light intensity of the first light signal detected by each of the detectors 120.

Figure 3C:
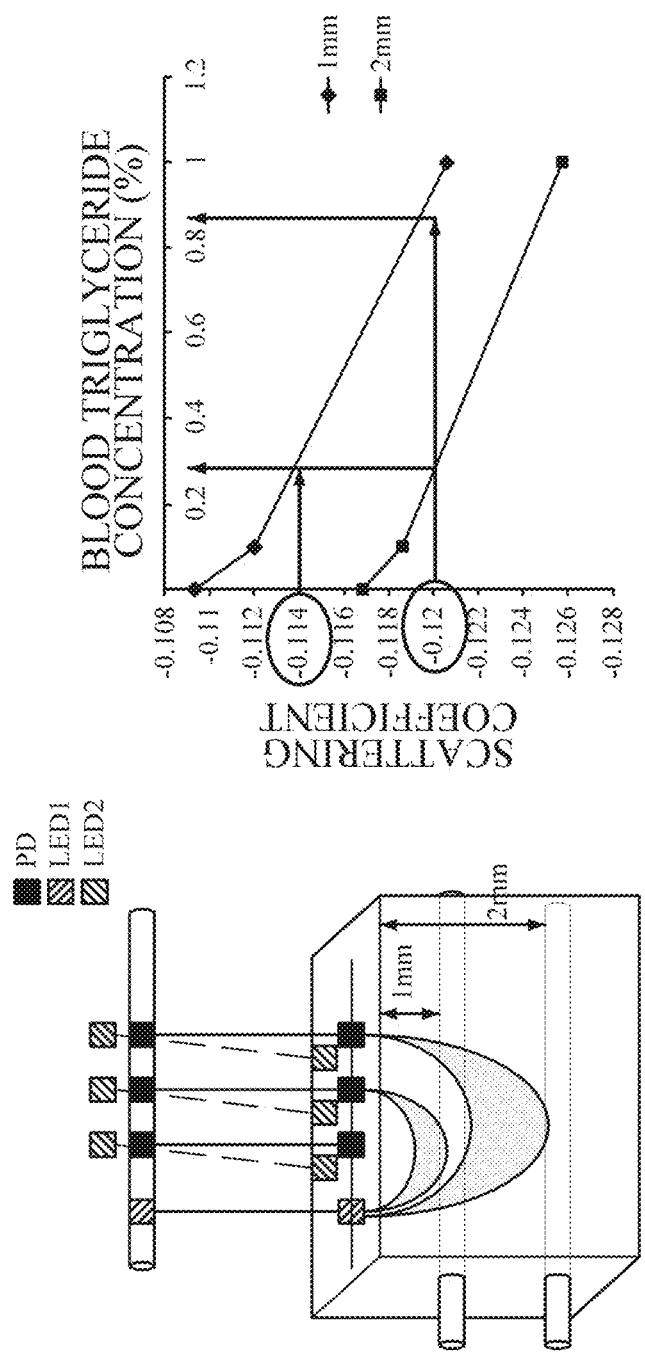
FIG. 3C is a diagram explaining a change in scattering coefficient according to a change in blood vessel depth and a change in concentration according to an exemplary embodiment.

FIG. 3C is a diagram explaining a change in scattering coefficient according to a change in blood vessel depth and a change in concentration according to an exemplary embodiment.

Referring to FIG. 3C, a scattering coefficient, which is changed according to a change in blood triglyceride concentration, may vary depending on the depth of blood vessels.

For example, assuming that a scattering coefficient value calculated at a time $t_1$ and a measurement point A is −0.114, and a scattering coefficient value calculated at a time $t_2$ and a measurement point A is −0.12 after a predetermined time elapses from the time $t_1$, it is difficult to determine whether a difference between the scattering coefficient value calculated at a time $t_1$ and the scattering coefficient value calculated at a time $t_2$ is caused by an increase in a triglyceride level from about 0.27% to about 0.85% with the same blood vessel depth of 1 mm, or is caused by only a change in blood vessel depth from 1 mm to 2 mm due to movement of an object and the like with no actual change in blood triglyceride concentration. Accordingly, the blood triglyceride concentration may not be estimated accurately.

For convenience of explanation, FIG. 3C illustrates an example of a change in scattering coefficient values calculated at the same measurement point A, but the same may also apply to a case where the measurement point at the time $t_2$ is changed to, for example, a measurement point B which is different from the measurement point A.

In this case, the processor 130 may correct the calculated scattering coefficient by using the blood vessel depth information.

For example, the processor 130 may generate blood vessel depth information based on a reflected light intensity of light which is reflected after being emitted by the second light source 111.

For example, when the second light source 111 emits light in a red light region (e.g., light in a wavelength range of 630 nm to 780 nm) onto an object, the reflected light intensity is changed by 0.07 V/mm according to a change in blood vessel depth, while the reflected light intensity is changed by 0.002 V/0.1% according to a change in triglyceride concentration.

That is, when the second light source 111 emits the light in the red light region, the reflected light intensity is changed more sensitively to a change in blood vessel depth than to a change in concentration of a biological component. Accordingly, the processor 130 may generate blood vessel depth information based on a change in light intensity of the second light signal (e.g., reflected light signal) which is reflected from the blood vessels of an object after being emitted by the second light source 111.

The processor 130 may determine a detection depth of the first light signal which is detected based on the blood vessel depth information, and may correct the calculated scattering coefficient based on a result of comparison of the determined detection depth with a reference depth.

Here, the reference depth may refer to a depth of blood vessels located at the shallowest depth from the surface of an object in the generated blood vessel depth information. However, the reference depth is not limited thereto, and may be a predetermined depth (e.g., 3 mm, etc.).

Further, the detection depth may refer to a depth of blood vessels from which the first light signal is obtained. For example, in the case where the first light source 110, the second light source 111, and the detector 120 are arranged along the blood vessels, the detection depth may refer to a depth of blood vessels at a position of the detector 120 which detects the first light signal.

In the case where the detection depth of the first light signal is different from the reference depth, the processor 130 may correct the scattering coefficient, calculated at the detection depth, to a scattering coefficient at the reference depth.

For example, in the case where the detection depth is greater than the reference depth, an intensity of a light signal detected by the detector 120 may be less than an intensity of a light signal detected at the reference depth, such that the processor 130 may correct the calculated scattering coefficient by adding a positive correction value to the scattering coefficient. By contrast, in the case where the detection depth is less than the reference depth, the intensity of the light signal detected by the detector 120 may be greater than the intensity of the light signal detected at the reference depth, such that the processor 130 may correct the calculated scattering coefficient by adding a negative correction value to the scattering coefficient.

As described above, by correcting the scattering coefficient, detected at the detection depth, to the scattering coefficient at the reference depth based on the blood vessel depth information, accuracy and reliability in measuring biological components may be guaranteed even when scattering coefficients are measured at different detection depths according to a user's activity during measurement of a biological component, a health state, a lapse of time, and a change in measurement point.

Referring back to FIG. 3C, in the case where a scattering coefficient value calculated at the time $t_1$ and the measurement point A is −0.114, and a scattering coefficient value calculated at the time $t_2$ and the measurement point A is −0.12 after a predetermined lapse of time, the processor 130 may determine, based on the blood vessel depth information, that the scattering coefficient calculated at the time $t_1$ and the measurement point A is calculated based on the first light signal scattered from the blood vessels located at the depth of 1 mm from the surface of an object; and the scattering coefficient calculated after a predetermined lapse of time at the time $t_2$ and the measurement point A is calculated based on the first light signal scattered from the blood vessels located at the depth of 2 mm from the surface of an object.

Accordingly, the processor 130 may determine that the blood triglyceride concentration is actually changed according to the depth of blood vessels, and may correct the calculated scattering coefficient at the time $t_2$ based on the blood vessel depth information.

For example, in the case where scattering coefficient values respectively calculated at times $t_1$ and $t_2$ and the measurement point A are −0.22 and −0.24, and blood vessel depths are 1 mm and 3 mm respectively, the processor 130 may convert the scattering coefficient value of 0.24, which is calculated at the time $t_2$ and at the blood vessel depth of 3 mm, to a scattering coefficient value calculated at the blood vessel depth of 1 mm. For example, by adding a correction value of 0.02 according to the depth of blood vessels to the scattering coefficient value calculated at the blood vessel depth of 3 mm based on the blood vessel depth information, the processor 130 may correct the scattering coefficient value, calculated at the time $t_2$ and at the blood vessel depth of 3 mm, to the scattering coefficient value calculated at the blood vessel depth of 1 mm.

In another example, in the case where scattering coefficient values respectively calculated at times $t_1$ and $t_2$ and the measurement point A are −0.22 and −0.24, and the blood vessel depth is 1 mm, the processor 130 may determine that the scattering coefficient values are calculated at the same blood vessel depth based on the scattered light intensity, and may determine that a change in scattering coefficient is caused by a change in concentration of a biological component. In this case, the processor 130 may measure the concentration of the biological component without correcting the calculated scattering coefficient, and thus may measure the biological component more accurately.

In addition, the processor 130 may select at least one detector based on a light intensity of the detected light signal, a signal to noise ratio (SNR), a distance between the first light source and each detector, and the blood vessel depth information.

In the case where a plurality of first light sources 110, second light sources 111, and detectors 120 are provided or are arranged in a predetermined array structure, the processor 130 may align the first light source 110 and the detector 120 along the blood vessels, and may select at least some of the plurality of first light sources 110 and detectors 130 to drive or select only the first light source 110 and the detector 130 located at a position of blood vessels of the same depth.

For example, the processor 130 may select at least one or more detectors from among a plurality of detectors 120 based on a light intensity of the detected first light signal. In this case, the processor 130 may calculate the light intensity of the first light signal detected by each of the plurality of detectors 130, and may select some of the detectors 130 with the highest light intensities.

In another example, the processor 130 may individually control the first light source 110, the second light source 111, and the detector 120 to calculate a signal to noise ratio of the light signal detected by the detector 120. When a plurality of first light sources 110, second light sources 111, and detectors 120 are disposed in the biological component measuring apparatus 100, the processor 130 may select at least one or more first light sources 110 and detectors 120 in order of magnitudes of the SNR. For example, the processor 130 may only drive any one of the first light sources 110 and any one of the detectors 120, to calculate an SNR of the first light signal, which is detected by each of the detectors for any one of the first light sources 110, and may determine an order of magnitudes of the SNR based on good signal characteristics, and may select at least one or more first light sources and detectors in the determined order of magnitudes of the SNR.

Further, instead of calculating the SNR of each detector 120 for any one of the first light sources 110, the processor 130 may calculate the SNR of each of the first light sources 110 for any one of the detectors 120 by sequentially driving the first light sources 110 for any one of the detector 120, and may select at least one or more first light sources 110 and detectors 120 in order of magnitudes of the calculated SNR.

For example, when the biological component measuring apparatus 100 includes a plurality of light sources 110a and a plurality of detectors 120a to form a plurality of light source/detector pairs 121 as shown in FIG. 3C, the processor 130 may discretely and sequentially turn on the light source/detector pairs 121 and select one of the light source/detector pairs 121 which has the highest SNR, or one or more of the light source/detector pairs 121 which exceed a predetermined SNR value.

In yet another example, with reference to FIGS. 1, 2, 3A, and 3B, the processor 130 may select at least one detector 120 based on a distance between the first light source 110 and the detectors 120. For example, the processor 130 may sequentially select two detectors 120 in short-distance order from the first light source 110, but is not limited thereto, and the processor 130 may select a detector 120 disposed at the shortest distance from the first light source 110 and a detector disposed at the longest distance from the first light source 110.

In still another example, the processor 130 may select at least two or more detectors 120 disposed at the position of blood vessels of the same depth from among a plurality of detectors 120.

Upon selecting at least one or more first light sources 110, second light sources 111, and detectors 120 from among the plurality of first light sources 110, second light sources 111, and detectors 120, the processor 130 may detect a light signal by driving only the selected first light sources 110, second light sources 111, and detectors 120, and may calculate a scattering coefficient based on the detected light signal.

For example, by detecting the first light signal by using only the first light sources 111 and the detectors 120 which are selected based on the highest light intensity, the SNR, and/or the distance between the first light source 111 and the detector 120, the processor 130 may calculate the scattering coefficient based on the detected first light signal.

Further, by calculating the scattering coefficient based on the first light signal detected by at least two or more detectors 120 disposed at the position of blood vessels of the same depth, the processor 130 may correct reliability of the calculated scattering coefficient.

The processor 130 may measure a biological component based on the calculated scattering coefficient. For example, based on a magnitude of a scattered light intensity of light which is scattered by a biological component contained in the blood of the blood vessels, the processor 130 may measure the concentration of a biological component. In this case, the concentration of a biological component to be measured in the blood may be proportional to the concentration of the scattering coefficient, such that the processor 130 may measure the concentration of a biological component according to a change in scattering coefficient.

In this case, the processor 130 may measure the concentration of a biological component based on a biological component estimation model, which is pre-generated based on the types of biological component to be measured, a measurement point, a correlation between the blood vessel depth information and the scattering coefficient, or by machine learning.

Further, the biological component estimation model may be an estimation model generated by at least one or more groups based on user characteristic information including at least one of race, gender, age, weight, percentage body fat, and body mass index (BMI), and health information including at least one of hepatocirrhosis, diabetes, and hyperlipidemia.

Figure 3D:
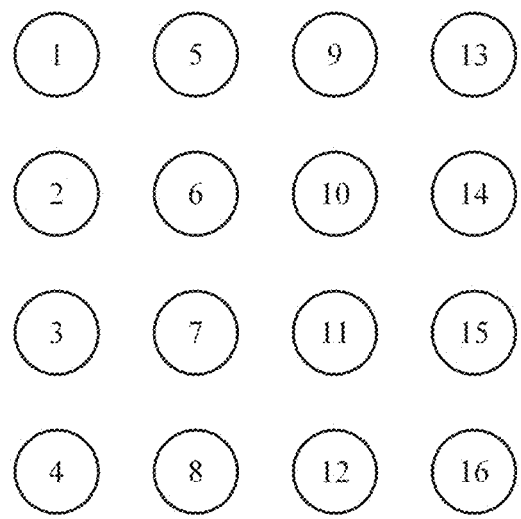
FIG. 3D illustrates an arrangement of light sources and detectors according to an exemplary embodiment.

FIGS. 3D and 3F illustrate arrangements of light sources and detectors according to various exemplary embodiments.

Figure 3E:
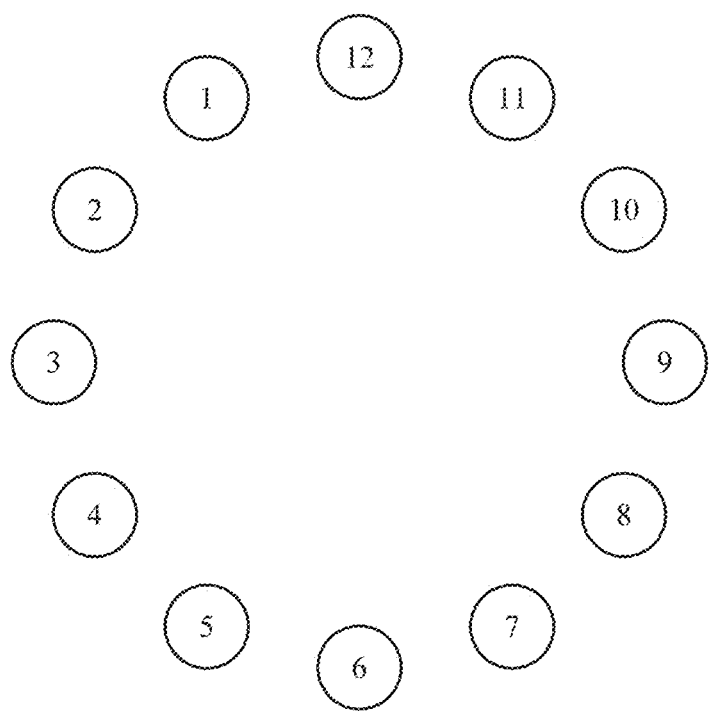
FIG. 3E illustrates an arrangement of light source and detector according to another exemplary embodiment.

As shown in FIGS. 3D and 3E, the first light source 110 and the detector 120 may include a plurality of first sub-light sources and a plurality of sub-detectors, respectively. The plurality of first sub-light sources and the plurality of sub-detectors are paired with each other in a one-to-one relationship so that each measurement unit 1-16 in FIG. 3D and each measurement unit 1-12 in 3F includes a pair of a first sub-light source and a sub-detector.

With reference to FIG. 3D, the processor 120 may select one of the measurement unit 1-16 which has the highest signal-to-noise ratio (SNR) or one or more measurement units 1-16 which exceed a predetermined SNR, and may determine that the selected measurement unit(s) is disposed to be aligned with a blood vessel. The processor 120 may measure the SNR based on a light intensity emitted from a first sub-light source and a light intensity received by a paired sub-detector. The processor 120 may turn on the selected measurement unit(s) and turn off the rest of the measurement units 1-16 so to collect a biological signal only from the selected measurement unit(s).

With reference to FIG. 3E, the processor 120 may select one of the measurement unit 1-12 which has the highest signal-to-noise ratio (SNR) or one or more measurement units 1-12 which exceed a predetermined SNR, and may determine that the selected measurement unit(s) is disposed to be aligned with a blood vessel. The processor 120 may measure the SNR based on a light intensity emitted from a first sub-light source and a light intensity received by a paired sub-detector. The processor 120 may turn on the selected measurement unit(s) and turn off the rest of the measurement units 1-12 so to collect a biological signal only from the selected measurement unit(s)

Figure 4:
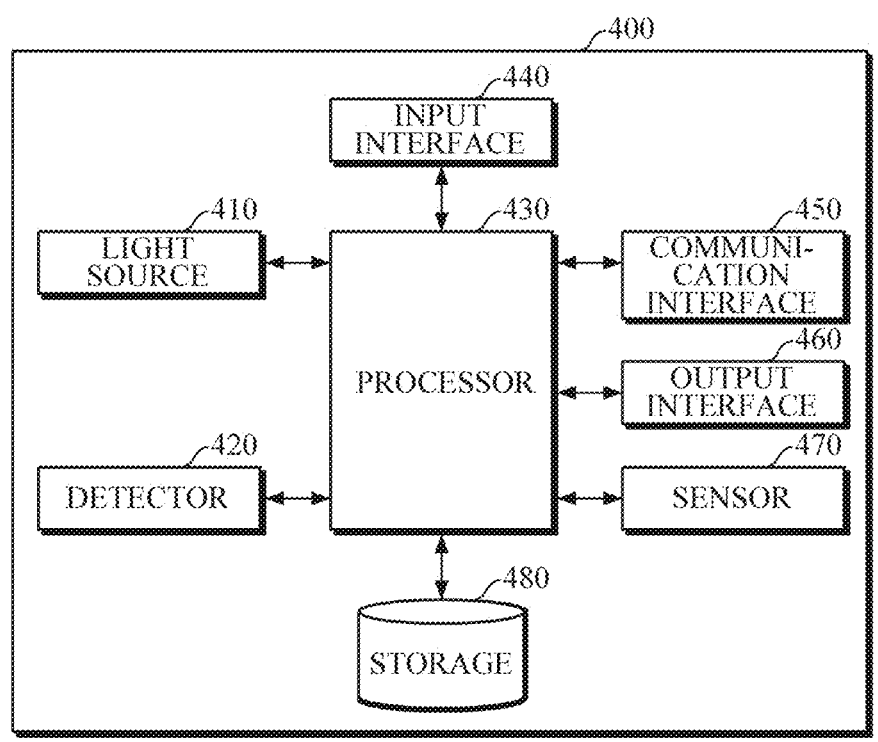
FIG. 4 illustrates a biological component measuring apparatus according to another exemplary embodiment.

FIG. 4 illustrates a biological component measuring apparatus according to another exemplary embodiment. Referring to FIG. 4, the biological component measuring apparatus 400 includes a light source 410, a detector 420, a processor 430, an input interface 440, a communication interface 450, an output interface 460, a sensor 470, and a storage 480. In this case, a plurality of light sources 410 may be included, which may be configured substantially in the same manner as, for example, the first light source 110 and the second light source 111 illustrated in FIG. 1, and the detector 420 and the processor 430 may be configured substantially in the same manner as the detector 120 and the processor 130 of the biological component measuring apparatus 100 of FIG. 1, such that the following description will be made based on details that do not overlap.

The input interface 430 may receive input of various operation signals and data that may be used in measuring a biological component from a user.

For example, the input interface 430 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

In addition, the input interface 430 may receive input of user characteristic information including at least one of race, gender, age, weight, percentage body fat, and body mass index (BMI), health information including at least one of hepatocirrhosis, diabetes, and hyperlipidemia, and information related to a biological component to be measured.

The communication interface 450 may be connected to an external device through a wired and wireless network according to a control signal of the processor 430, and may transmit and receive a measurement result of a biological component to and from the external device.

In this case, the external device may be medical equipment using a blood vessel depth and a biological component estimation model database (DB), and/or the measured biological component, a printer to print out results, or a display to display the measurement result of the biological component. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

For example, the communication interface 450 may be one or more modules which perform communication by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. Further, examples of the external device may include a mobile terminal such as a smartphone, a tablet PC, a mobile communication terminal, and the like, or a desktop computer, a laptop computer, and the like.

Instead of detecting a light signal by using the light source 410 and the detector 420 of the biological component measuring apparatus 400, the processor 430 may obtain information related to the light signal from an external device through the communication interface 450. In this case, the processor 430 may control the communication interface 450 to receive information related to the light signal of an object from an external light signal detecting device.

The output interface 460 may output at least one of an operation state of the light source 410 and the detector 420, the position and depth of blood vessels, a scattered light intensity, a reflected light intensity, the types and concentration of a biological component, guide information, and warning information, or may output various types of information including a data transmission and reception state of the communication interface 450.

For example, the output interface 460 may be a touchable display including a user interface (UI), which may display the generated blood vessel depth information, a measurement result of a bio-signal, and information on whether to correct a scattering coefficient of the processor 430 in divided display areas, and may display a biological component to be measured and detailed information of a user.

However, the output interface 460 is not limited thereto, and may display various types of information by using a non-visual method such as acoustic method (e.g., voice alarm, etc.) and a tactility method (e.g., vibration, etc.).

In addition, the output interface 460 may output a guide image when the light source 410 and the detector 420 are in poor contact with each other or in order to guide a measurement point for measuring a biological component, or may output warning information when the measured biological component exceeds a critical level.

For example, in the case where the measured triglyceride level exceeds 200 mg/dL, the output interface 460 may display warning information such as "risk alert".

The sensor 470 may sense a change in a measurement position of an object. For example, in the case where the biological component measuring apparatus 400 is embedded in a mobile terminal or a wearable device, a light emitting position of the light source 410 and/or a light signal detecting position of the detector 420 for measuring a biological component may be changed by movement of a user, user's changes, and the like. In the case where the position of the light source 410 and/or the detector 420 falls outside a predetermined threshold range, the sensor 470 may sense that a measurement position of the object is changed.

For example, in the case where the biological component measuring apparatus 400 is embedded in a wearable device (e.g., smart watch) which is worn on the wrist, the sensor 470 may sense an initial position; and upon sensing a change in position which is outside the radius of 1 cm from the center of the sensed initial position, the sensor 470 may sense that the measurement position of the object is changed. In this case, the sensor 470 may include at least one of an acceleration sensor, a gyro Sensor, a motion sensor, a displacement sensor, a pressure sensor, a proximity sensor, a G-sensor, and an image sensor, but is not limited thereto.

Once the sensor 470 senses that the measurement position of the object is changed, the processor 430 may re-generate blood vessel depth information. That is, at the time of initialization of the biological component measuring apparatus 400, the processor 470 may detect a biological component of an object by selecting a measurement position of the object and by selecting at least one or more light sources and detectors from among a plurality of light sources 410 and detectors 420; and when the measurement position of the object is changed, the processor 470 may re-generate the blood vessel depth information, or may re-select at least one or more light sources and detectors from among the plurality of light sources 410 and detectors 420.

The storage 480 may store various types of information including an output state (e.g., a power on/off state, wavelength band, etc.), an arrangement of the detector 420 (e.g., array, etc.), the light intensity of a light signal detected by the detector 420, an SNR, a measurement result of a biological component by using the selected light sources and/or detectors, and a data transmission and reception state of the communication interface 450.

For example, the storage 480 may categorize measurement results according to biological components of the object, and may store a biological component estimation model generated by one or more groups.

In this case, the storage 480 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 5:
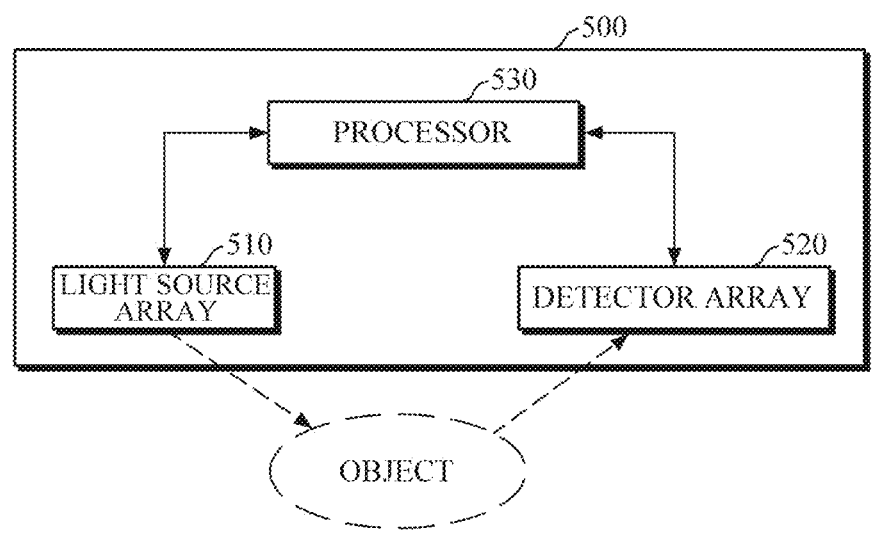
FIG. 5 illustrates a biological component measuring apparatus according to another exemplary embodiment.

FIG. 5 illustrates a biological component measuring apparatus 500 according to another exemplary embodiment. The biological component measuring apparatus 500 of FIG. 5 includes a light source array 510, a detector array 520, and a processor 530.

Referring to FIG. 5, the light source array 510 may emit light onto an object.

The light source array 510 may be multiple light sources including one or more light sources which emit light in a specific wavelength band of visible light, or emit light in the near infrared range or the mid infrared range.

For example, the light source array 510 may include at least one or more first light sources and second light sources in which the first light sources emit light in the near infrared range, and the second light sources emit light in a specific wavelength region (e.g., light in a Green to Infrared region in a wavelength range of 500 nm to 855 nm, etc.). Further, the light source array 510 may be one or more light sources configured as an independent module, and each of the light sources may be controlled individually by the processor 530 to emit light of different wavelength bands.

However, the light source array 510 is not limited thereto, and may be configured as a single physical module, or may be configured to repeatedly and sequentially emit light in multiple wavelength bands.

The detector array 520 may detect a light signal emitted by each of the light sources of the light source array 510.

For example, the detector array 520 may detect, as a light signal, at least one of reflected light which is reflected from an object, absorbed light which is absorbed into the object, and scattered light which is scattered from a biological component, after light is emitted from the light source array 520. Further, the detector array 520 may include one or more detectors, and may be arranged in a predetermined array structure.

For example, each of the light sources of the light source array 510 and each of the detectors of the detector array 520 may be arranged in a predetermined array structure having a shape among a square shape, a circular shape, a concentric circular shape, and a band shape. However, the structure is not limited thereto, and the distance between each of the light sources of the light source array 510 and each of the detectors of the detector array 520 may be determined arbitrarily and irregularly.

Hereinafter, for convenience of explanation, the light signal may refer to a light signal of scattered light which is scattered from a biological component after being emitted by the light sources of the light source array 510 and is detected by one or more detectors of the detector array 520.

The processor 530 may individually control each of the light sources of the light source array 510 and each of the detectors of the detector array 520 to drive at least one light source and detector.

For example, the processor 530 may sequentially drive each of the light sources of the light source array 510 and each of the detectors of the detector array 520 to drive the light source and the detector as a one-to-one combination, and may individually drive the light source and the detector to drive the light source and the detector as a many-to-one combination.

In addition, the processor 530 may drive each of the light sources of the light source array 510 and each of the detectors of the detector array 520 according to a predetermined light source-detector driving pattern.

The processor 530 may generate light path length information between the detector and blood vessels based on a change in light signal, detected by a driven detector, according to depths of blood vessels.

Figure 6:
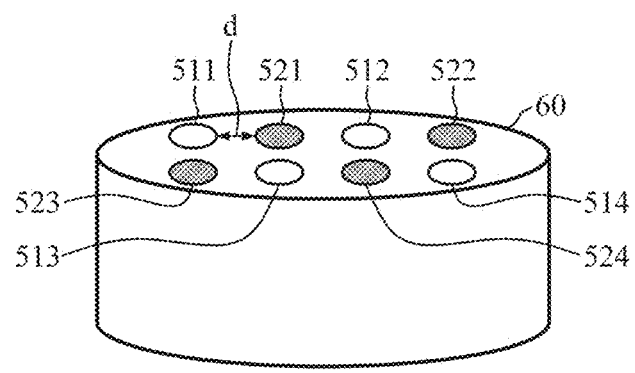
FIG. 6 illustrates an example of an arrangement of light sources of a light source array and detectors of a detector array according to an exemplary embodiment.

FIG. 6 illustrates an arrangement of light sources of a light source array and detectors of a detector array according to an exemplary embodiment.

Referring to FIGS. 5 and 6, the light sources 511, 512, 513, and 514 of the light source array 510, and the detectors 521, 522, 523, and 524 of the detector array 520 may be spaced apart at equal intervals in a band shape on a probe 60.

For example, while driving the detector 521, the processor 530 may sequentially drive the light sources 511, 512, 513, and 514, and may generate light path length information based on a distance d between the driven light sources 511, 512, 513, and 514 and the detector 521 and a change in intensity of a light signal detected by the detector 521.

For example, the driven detector 521 is spaced apart by the same distance d from some light sources 511, 512, and 513, and is disposed at a longer distance from the light source 514, among the light sources 511, 512, 513, and 514. In this case, the processor 530 may calculate the light path length for blood vessels based on a change in light intensity of reflected light which is reflected from an object after being emitted by some light sources 511, 512, and 513 which are spaced apart by the same distance from the detector 521.

That is, in the case where there is a difference in light intensity of reflected light which is reflected from an object after being emitted by some light sources 511, 512, and 513 which are spaced apart by the same distance from the detector 521, the processor 530 may determine that a light path length becomes shorter as the detected light intensity is increased, and may generate the light path length information between each light source of the light source array 510 and each detector of the detector array 520 based on the detected light intensity.

In other words, as the blood vessels are disposed at a longer distance from each of the light sources 511, 512, 513, and 514 of the light source array 510 or each of the detectors 521, 522, 523, and 524 of the detector array 520, or as the blood vessels are located at a greater depth from the surface of an object, the light intensity detected by each of the detectors 521, 522, 523, and 524 is exponentially decreased, such that a change in depth of blood vessels leads to a change in light intensity, and the processor 530 may generate the light path length information based on the change in light intensity.

In another example, in the case where the light source array 510 include one or more first light sources which emit light in a near infrared region, and a second light source which emits light in a specific wavelength region (e.g., light in a Green to Infrared region in a wavelength range of 500 nm to 855 nm, etc.), the processor 530 may generate light path length information based on the light intensity of a light signal detected by a driven detector and a distance between the driven detector and the second light source.

Further, for each of the detectors 521, 522, 523, and 524 of the detector array 520, the processor 530 may sequentially drive the light sources 511, 512, 513, and 514 of the light source array 510, to calculate a light path length of each of the detectors 521, 522, 523, and 524 for the blood vessels.

The processor 530 may measure a biological component by correcting a scattering coefficient based on the generated light path length information.

For example, the processor 530 may calculate the scattering coefficient based on the light intensity of the light signal detected by the detector array 520, and a distance between the driven detector of the detector array 520 and the driven light source of the light source array 510.

In this case, upon calculating the light path length information, the processor 530 may compare the light path length for the detected light signal with a predetermined reference length, and may correct the calculated scattering coefficient to a scattering coefficient calculated at the reference length. Here, the reference length may be determined to be the shortest light path length based on the light path length information, but is not limited thereto, and may be a predetermined light path length (e.g., 4 mm, etc.)

As described above, by correcting the calculated scattering coefficient to a scattering coefficient at the reference length based on the light path length information for the blood vessels, accuracy and reliability in measuring biological components may be guaranteed even when scattering coefficients are measured at different light path lengths according to a user's activity during measurement of a biological component, a health state, a lapse of time, and a change in measurement point.

In another example, the processor 530 may determine a detection depth of the first light signal based on the light path length information, and may correct the calculated scattering coefficient based on a result of comparison of the determined detection depth with a reference depth. For example, as blood vessels are disposed at greater depths from the surface of an object, or as blood vessels are located at a longer distance from the driven light source of the light source array 510 or the driven detector of the detector array 520, the light path length may be increased; and in the case where the detection depth of the light signal is different from the reference depth, the processor 530 may correct the scattering coefficient calculated at the detection depth to the scattering coefficient at the reference depth.

For example, in the case where the detection depth is deeper than the reference depth, the intensity of a light signal detected by the detector array 520 may be less than the intensity of a light signal detected at the reference depth, such that the processor 530 may correct the calculated scattering coefficient by adding a positive correction value to the scattering coefficient. By contrast, in the case where the detection depth is shallower than the reference depth, the intensity of a light signal detected by the detector array 520 may be greater than the intensity of a light signal detected at the reference depth, such that the processor 530 may correct the calculated scattering coefficient by adding a negative correction value to the scattering coefficient.

In yet another example, the processor 530 may select at least two or more detectors, having the same light path length, from among a plurality of detectors based on the light path length information, and may calculate a scattering coefficient based on the first light signal detected by the selected detectors.

For example, by individually controlling the light source array 510 and the detector array 520 to calculate each light path length of a light signal which is emitted by each light source of the light source array 510 and is detected by each detector of the detector array 520, the processor 530 may select detectors having the same light path length. In this case, by driving only the light sources and the detectors having the same light path length to detect the light signal, the processor 530 may guarantee reliability of the calculated scattering coefficient.

The processor 530 may measure a biological component based on the calculated scattering coefficient. For example, based on a magnitude of a scattered light intensity of light which is scattered by a biological component contained in the blood of the blood vessels, the processor 530 may measure the concentration of a biological component. In this case, the concentration of a biological component to be measured in the blood may be proportional to the concentration of the scattering coefficient, such that the processor 530 may measure the concentration of a biological component according to a change in scattering coefficient.

Figure 7:
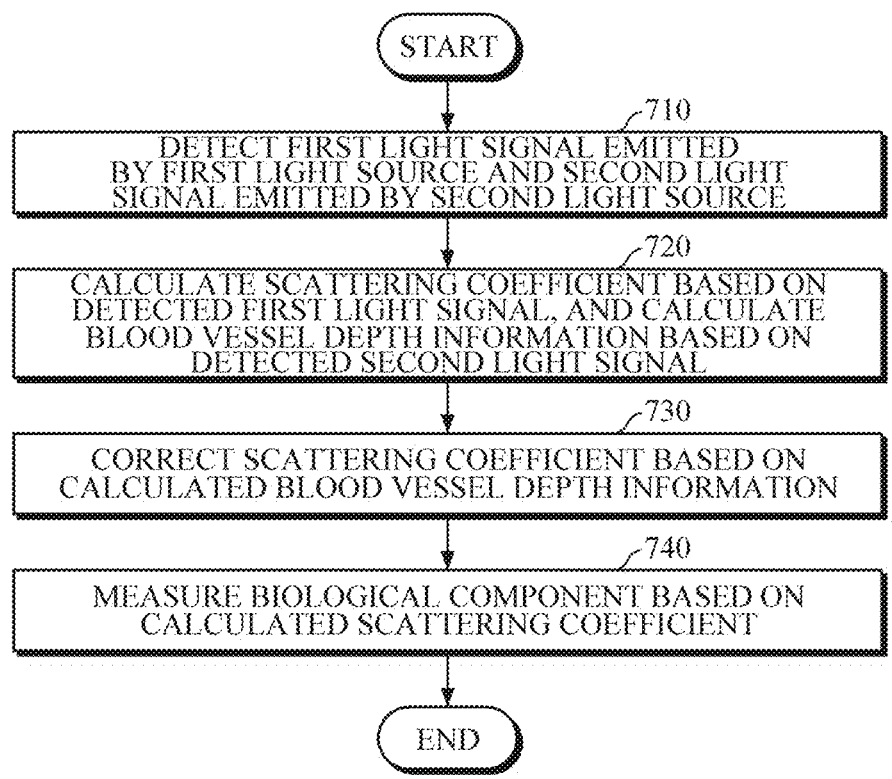
FIG. 7 is a flowchart illustrating a biological component measuring method according to an exemplary embodiment.

FIG. 7 is a flowchart illustrating a biological component measuring method according to an exemplary embodiment. The biological component measuring method of FIG. 7 may be performed by the biological component measuring apparatuses 100 and 400 illustrated in FIGS. 1 and 4.

The biological component measuring apparatus 100 may detect a first light signal emitted by the first light source 110 and a second light signal emitted by the second light source 111 in operation 710.

For example, the biological component measuring apparatus 100 includes the first light source 110 and the second light source 111 which may emit light onto an object. In this case, the first light source 110 and the second light source 111 may emit light in a specific wavelength band of visible light and may emit light in the near infrared range or the mid infrared range. For example, the first light source 110 may emit light in the near infrared range, and the second light source 111 may emit light in a specific wavelength region (e.g., light in a Green to Infrared region in a wavelength range of 500 nm to 855 nm, etc.), e.g., a red light region (i.e., light in a wavelength range of 630 nm to 780 nm, etc.).

The biological component measuring apparatus 100 may detect, as a light signal, at least one of reflected light which is reflected from skin of an object, absorbed light which is absorbed into the skin, and scattered light which is scattered from a biological component, after light is emitted from the first light source 110 and the second light source 111.

In this case, the biological component measuring apparatus 100 may detect the first light signal by using the first light source 110 and the detector 120 which are disposed on the surface of an object to be aligned with a position of the blood vessels. For example, the first light source 110 may be arranged side by side along the blood vessels on the surface of the object, and the detector 120 may be arranged side by side along the blood vessels at a position spaced apart by a predetermined distance from the first light source 110.

The biological component measuring apparatus 100 may calculate a scattering coefficient based on the detected first light signal, and may calculate blood vessel depth information based on the detected second light signal in operation 720.

For example, when the detector 120 includes a first detector and a second detector, the biological component measuring apparatus 100 may calculate the scattering coefficient based on the light intensity of the first light signal and distances $\rho_1, \rho_2$ between the first light source 110 and each of the first detector and the second detector which are disposed at different distances from the first light source 110.

Further, the biological component measuring apparatus 100 may generate blood vessel depth information based on the light intensity of reflected light which is reflected after being emitted by the second light source 111.

For example, in the case where the second light source of the biological component measuring apparatus 100 emits light in a specific wavelength region (e.g., light in a Green to Infrared region in a wavelength range of 500 nm to 855 nm, etc.) onto an object, the biological component measuring apparatus 100 may generate blood vessel depth information based on a change in reflected light intensity according to a change in depth of blood vessels.

For example, when second light source emits light in a red light region (e.g., light in a wavelength range of 630 nm to 780 nm), the reflected light intensity is changed more sensitively to a change in blood vessel depth than to a change in concentration of a biological component. Accordingly, the biological component measuring apparatus 100 may generate blood vessel depth information based on a change in light intensity of the second light signal which is reflected from the blood vessels of an object after being emitted by the second light source.

Then, the biological component measuring apparatus 100 may correct a scattering coefficient based on the calculated blood vessel depth information in operation 730.

For example, the biological component measuring apparatus 100 may determine a detection depth of the detected first light signal based on the blood vessel depth information, and may correct the calculated scattering coefficient based on a result of comparison of the determined detection depth and a reference depth.

In the case where the detection depth of the first light signal is different from the reference depth, the biological component measuring apparatus 100 may correct a scattering coefficient, calculated at the detection depth, to a scattering coefficient at the reference depth.

As described above, by correcting the scattering coefficient, detected at the detection depth, to the scattering coefficient at the reference depth based on the blood vessel depth information, accuracy and reliability in measuring biological components may be guaranteed even when scattering coefficients are measured at different detection depths according to a user's activity during measurement of a biological component, a health state, a lapse of time, and a change in measurement point.

Further, the biological component measuring apparatus 100 may select at least one detector based on a light intensity of the detected light signal, a signal to noise ratio (SNR), a distance between the first light source and each detector, and the blood vessel depth information.

For example, in the case where a plurality of first light sources 110, second light sources 111, and detectors 120 are provided or are arranged in a predetermined array structure, the biological component measuring apparatus 100 may align the first light source 110 and the detector 120 along the blood vessels, and may select at least some of the plurality of first light sources 110 and detectors 130 to drive or select only the first light source 110 and the detector 130 located at a position of blood vessels of the same depth.

In another example, by individually controlling the first light sources, the second light sources, and the detectors to calculate a signal to noise ratio (SNR) of the light signal detected by the detector, and the biological component measuring apparatus 100 may select at least one or more first light sources and detectors in order of magnitudes of the SNR. For example, in the case where a plurality of first light sources 110, second light sources 111, and detectors 120 are disposed, the biological component measuring apparatus 100 may only drive any one of the first light sources 110 and any one of the detectors 120, to calculate an SNR of the first light signal, which is detected by each of the detectors for any one of the first light sources 110, and may determine an order of magnitudes of the SNR based on good signal characteristics, and may select at least one or more first light sources and detectors in the determined order of magnitudes of the SNR.

In yet another example, the biological component measuring apparatus 100 may select at least two or more detectors, disposed at a position of blood vessels of the same depth, from among a plurality of detectors.

Upon selecting at least one or more first light sources 110, second light sources 111, and detectors 120 from among the plurality of first light sources 110, second light sources 111, and detectors 120, the biological component measuring apparatus 100 may detect a light signal by driving only the selected first light sources 110, second light sources 111, and detectors 120, and may calculate a scattering coefficient based on the detected light signal.

For example, by detecting the first light signal by using the first light sources and the detectors which are selected based on the highest light intensity, the SNR, and the distance between the first light source and the detector, the biological component measuring apparatus 100 may calculate the scattering coefficient based on the first light signal having good signal characteristics.

Further, by calculating the scattering coefficient based on the first light signal detected by at least two or more detectors disposed at a position of blood vessels of the same depth, the biological component measuring apparatus 100 may guarantee reliability of the calculated scattering coefficient.

The biological component measuring apparatus 100 may measure a biological component based on the calculated scattering coefficient in operation 740.

Based on a magnitude of a scattered light intensity of light which is scattered by a biological component contained in the blood of the blood vessels, the biological component measuring apparatus 100 may measure the concentration of a biological component. In this case, the concentration of a biological component to be measured in the blood may be proportional to the concentration of the scattering coefficient, such that the biological component measuring apparatus 100 may measure the concentration of a biological component according to a change in scattering coefficient.

In this case, the biological component measuring apparatus 100 may measure the concentration of a biological component based on a biological component estimation model, which is pre-generated based on the types of biological component to be measured, a measurement point, a correlation between the blood vessel depth information and the scattering coefficient, or by machine learning.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biological component measuring apparatus comprising:
    a first light source configured to emit a first light of a first wavelength range onto an object;
    a plurality of second light sources configured to emit second lights of a second wavelength range onto the object, the second wavelength range being different from the first wavelength range;
    a plurality of detectors configured to detect the first light and the second lights which are scattered or reflected from the object; and
    a processor configured to determine a scattering coefficient based on the detected first light, obtain blood vessel depth information based on the detected second lights, and measure a concentration of a biological component by correcting the scattering coefficient based on the blood vessel depth information,
    wherein the plurality of second light sources are disposed to correspond to the plurality of detectors, respectively.

2. The biological component measuring apparatus of claim 1, wherein the first light source and the plurality of detectors are disposed on a surface of the object and aligned with a position of at least one blood vessel of the object.

3. The biological component measuring apparatus of claim 1, wherein the plurality of detectors are arranged in a line.

4. The biological component measuring apparatus of claim 3, wherein the first light source is disposed to be spaced apart on the extension line of the plurality of detectors.

5. The biological component measuring apparatus of claim 3, wherein the second light sources are placed a predetermined distance apart from the side of the line which the plurality of detectors are arranged in.

6. The biological component measuring apparatus of claim 1, wherein the processor is further configured to select one or more detectors of the plurality of detectors based on a light intensity of a plurality of first lights detected by the plurality of detectors, a signal to noise ratio (SNR) of the plurality of first lights, a distance between the first light source and each of the plurality of detectors, and blood vessel depth information for each of the plurality of detectors.

7. The biological component measuring apparatus of claim 6, wherein the processor is further configured to select the one or more detectors in response to determining that the one or more detectors are aligned with blood vessels having a same depth from a skin surface of the object.

8. The biological component measuring apparatus of claim 6, wherein the processor is further configured to determine the scattering coefficient based on first lights detected by the selected one or more detectors.

9. The biological component measuring apparatus of claim 6, wherein the processor is further configured to determine a signal to noise (SNR) ratio of the detected plurality of first lights, and select one or more detectors of the plurality of detectors in the order of magnitudes of the SNR.

10. The biological component measuring apparatus of claim 1, wherein the processor is further configured to determine a detection depth of the detected first light based on the blood vessel depth information, and correct the scattering coefficient based on a result of comparison of the detection depth with a reference depth.

11. The biological component measuring apparatus of claim 1, wherein the processor is further configured to determine a scattered light intensity based on the detected first light, and determine the scattering coefficient based on the scattered light intensity and a distance between the plurality of detectors and the first light source.

12. The biological component measuring apparatus of claim 1, wherein the processor is further configured to determine a reflected light intensity based on the detected second light, and generate the blood vessel depth information by estimating a change in a blood vessel depth according to a change in the reflected light intensity.

13. A biological component measuring method comprising:
    detecting, by a plurality of detectors, a first light signal emitted by a first light source;
    detecting, by the plurality of detectors, second light signals emitted by a plurality of second light sources;
    determining a scattering coefficient based on the detected first light signal;
    obtaining blood vessel depth information based on the detected second light signals;
    correcting the scattering coefficient based on the blood vessel depth information; and
    measuring a concentration of a biological component based on the corrected scattering coefficient,
    wherein the plurality of second light sources are disposed to correspond to the plurality of detectors, respectively.

14. The biological component measuring method of claim 13, wherein the first light source and the plurality of detectors are aligned with a position of at least one blood vessel.

15. The biological component measuring method of claim 13, wherein the plurality of detectors are arranged in a line.

16. The biological component measuring method of claim 15, wherein the first light source is disposed to be spaced apart on the extension line of the plurality of detectors.

17. The biological component measuring method of claim 15, wherein the second light sources are placed a predetermined distance apart from the side of the line which the plurality of detectors are arranged in.

18. The biological component measuring method of claim 13, wherein the correcting the scattering coefficient comprises:
determining a detection depth of the first light signal based on the blood vessel depth information; and
correcting the scattering coefficient based on a result of comparison of the detection depth with a reference depth.

19. The biological component measuring method of claim 13, wherein the determining the scattering coefficient comprises:
determining a scattered light intensity based on the first light signal; and
determining the scattering coefficient based on the scattered light intensity and a distance between the plurality of detectors and the first light source.

20. The biological component measuring method of claim 13, wherein the obtaining the blood vessel depth information comprises:
determining a reflected light intensity based on the detected second light signals; and
generating the blood vessel depth information by estimating a change in a blood vessel depth according to a change in the reflected light intensity.

* * * * *